(12) United States Patent
Kaczorowski et al.

(10) Patent No.: US 8,695,800 B2
(45) Date of Patent: Apr. 15, 2014

(54) HOLDING AND PACKAGING DEVICE FOR A TOOTH IMPLANT

(75) Inventors: Heiko Kaczorowski, Bad Liebenzell (DE); Ralph Hermann, Karlsruhe (DE)

(73) Assignee: inpac Medizintechnik GmbH, Birkenfeld (DE)

( * ) Notice: Subject to any disclaimer, the term of this patent is extended or adjusted under 35 U.S.C. 154(b) by 1096 days.

(21) Appl. No.: 12/349,739

(22) Filed: Jan. 7, 2009

(65) Prior Publication Data
US 2009/0200188 A1    Aug. 13, 2009

Related U.S. Application Data

(63) Continuation of application No. PCT/EP2007/006164, filed on Jul. 11, 2007.

(30) Foreign Application Priority Data

Jul. 12, 2006    (DE) .................. 10 2006 033 382

(51) Int. Cl.
    *A61C 19/02*    (2006.01)
(52) U.S. Cl.
    USPC ........................ 206/368; 206/63.5; 24/557
(58) Field of Classification Search
    USPC ............ 206/368, 369, 363, 570, 63.5, 438; 24/465, 456, 557, 552, 553, 554, 565
    See application file for complete search history.

(56) References Cited

U.S. PATENT DOCUMENTS

| | | | | |
|---|---|---|---|---|
| 2,195,967 A | * | 4/1940 | Liebmann | 24/72.5 |
| 4,471,512 A | * | 9/1984 | Thalenfeld | 24/557 |
| 4,722,120 A | * | 2/1988 | Lu | 24/489 |
| 5,048,159 A | * | 9/1991 | Johansson et al. | 24/20 R |
| 5,414,911 A | * | 5/1995 | Adams | 24/545 |
| 5,625,931 A | * | 5/1997 | Visser et al. | 24/557 |
| 6,261,097 B1 | | 7/2001 | Schmutz et al. | |
| 6,523,231 B1 | * | 2/2003 | Lassiter | 24/339 |
| 2004/0093702 A1 | * | 5/2004 | Mallicoat | 24/546 |
| 2004/0112781 A1 | | 6/2004 | Hofverberg et al. | |
| 2005/0035015 A1 | | 2/2005 | Bressler et al. | |
| 2006/0042050 A1 | * | 3/2006 | Misumi | 24/3.1 |

FOREIGN PATENT DOCUMENTS

| | | |
|---|---|---|
| EP | 0 986 341 B1 | 3/2000 |
| EP | 1 447 056 A2 | 8/2004 |
| JP | 2004-243127 | 9/2004 |

* cited by examiner

*Primary Examiner* — Steven A. Reynolds
(74) *Attorney, Agent, or Firm* — Harness, Dickey & Pierce, P.L.C.

(57) ABSTRACT

The invention relates to a holding and packaging device for a tooth implant, with an elongate cylindrical receiving element (12) which has a cylinder wall (14) and at least one end wall (16), wherein the end wall (16) has an opening (18) for receiving a tooth implant (50), and the cylinder wall has a longitudinal opening (20) in this region. It is proposed that the longitudinal opening (20) extends over the entire length of the cylinder wall (14), that at least two grip elements (22, 24) which are mounted opposite each other on the cylinder wall and extend outward are provided, and that the cylinder wall (14) is manufactured from an elastic material such that, by application of a force, the opening (18) in the end wall (16) can be widened in order to introduce or remove a tooth implant.

14 Claims, 4 Drawing Sheets

HOLDING AND PACKAGING DEVICE FOR A TOOTH IMPLANT

CROSSREFERENCES TO RELATED APPLICATIONS

This application is a continuation of copending international patent application PCT/EP2007/006164 filed on Jul. 11, 2007 and designating the U.S., which was published in German and claims priority of German patent application DE 10 2006 033 382.9 filed on Jul. 12, 2006. The entire contents of these applications are incorporated herein by reference.

BACKGROUND OF THE INVENTION

The present invention relates to a holding and packaging device for a dental or tooth implant, with an elongate cylindrical receiving element which has a cylinder wall and at least one end wall, wherein the end wall has an opening for receiving a tooth implant, and the cylinder wall has a longitudinal opening in this region.

A holding device of this type is known, for example, from the publication EP 0 986 341 B1. Said publication describes a holding element for an implant and an ampule for storing the implant. The cylindrical ampule serves to hold a dental implant such that it can be introduced into a larger packaging. The ampule has a cylinder casing which has a cutout through which the dental implant can be introduced into the internal space surrounded by the cylinder casing. In order to hold the dental implant in the ampule, a special holding element is connected to the dental implant, and said holding element is then inserted into an opening provided in an end wall of the ampule.

Among the disadvantages of said ampule is that the handling of the dental implant is not optimal and that an additional holding element has to be connected to the dental implant in order to hold the implant in the ampule.

Dental implants generally have a sensitive surface which must not be touched during manipulation, transportation and packaging. The implants are mounted with a fixing post which is screwed or clamped to a handling aid. Said handling aid frequently serves as a closure or closure stopper of a small glass receptacle which then also serves as the primary sterile packaging.

SUMMARY OF THE INVENTION

In general, one object of the present invention is to simplify the handling of a dental implant and the packaging thereof, wherein the simplification of the handling must not be a burden on the production costs.

This object is achieved in the case of the holding and packaging device mentioned at the beginning in that the longitudinal opening extends over the entire length of the cylinder wall, at least two grip elements which are mounted opposite each other on the cylinder wall and extend outward are provided, and the cylinder wall is manufactured from an elastic material such that, by application of a force, preferably via the grip elements, the opening in the end wall can be widened in order to introduce or remove a tooth implant.

That is to say, in other words, that the tooth implant is held in the cylindrical receiving element by clamping force, wherein said clamping force can be reduced, for example, by "actuation" of the grip elements or by direct manipulation of the tooth implant, in order to remove the tooth implant from the holding device. Consequently, the cylinder wall is manufactured in such a manner that it can be widened somewhat in order therefore to enlarge the receiving opening on the end wall, in which the dental implant is held. Said manipulation is possible without touching the dental implant. Furthermore, the holding and packaging device can also be readily deposited on a flat surface without the dental implant coming into contact with said surface.

On account of the simple construction of the holding and packaging device, manufacturing by injection molding is possible, thus enabling very cost-effective manufacturing.

In a preferred development, the cylinder wall in cross section encloses an angle of at least 180°, and the longitudinal opening in the circumferential direction is at least the same size as the diameter of the tooth implant to be inserted.

This measure has the advantage that the cylinder wall surrounds a large region such that the dental implant located within the cylinder wall is well protected against contact, etc.

In a preferred development, the grip elements are arranged on the cylinder wall in a manner such that they lie in one plane.

This configuration has proven particularly advantageous in practice. In particular, the holding device can therefore be deposited very securely on a smooth surface without the dental implant touching the surface.

In a preferred development, the opening in the end wall is designed in the shape of a circular segment and is open at the edge toward the longitudinal opening.

This measure has the advantage that the tooth implant can easily be placed into the opening. It should be noted here that the circular segment preferably extends over an angle of more than 180° such that the remaining gap is smaller than the diameter of the opening.

In a preferred development, the opening is arranged coaxially with respect to the longitudinal axis of the receiving element.

This measure has the advantage that, firstly, good clamping of the dental implant can be achieved and, secondly, the distance of the longitudinal axis from a supporting surface is of a size such that the dental implant does not touch the supporting surface.

In a preferred development, a slot lying opposite the longitudinal opening extends radially from the opening.

This measure has the advantage that the widening of the opening in order to release the clamping of the dental implant is made easier.

In a preferred development, the receiving element is manufactured from a flexible plastic, preferably a biocompatible plastic.

This has the advantage that the receiving element and consequently the entire holding and packaging device can be treated with all customary sterilization methods (radiation, gas, steam). Furthermore, the holder can be produced easily, for example by means of injection molding of plastic. Furthermore, the required elasticity necessary for the widening of the opening is obtained by using a plastic.

In addition—in contrast to previous solutions—it is possible to sterilize the holding and packaging device, which has been removed from the primary sterile packaging together with the dental implant accommodated in said device, once again with the customary methods.

In a preferred development, a further grip element which is arranged between the two other grip elements is provided. The grip elements preferably lie at an angle of 90° with respect to one another.

The handling of the holding device is further improved with the aid of the third grip element.

In a preferred development, a respective wall element is mounted on the two grip elements, said wall element extending perpendicularly with respect to the grip element and serving as a spacer element.

That is to say, in other words, that the distance of the inserted dental implant from a supporting surface is further increased by the two wall elements mounted on the grip elements, and therefore the risk of contact is correspondingly reduced. Furthermore, the protection of the dental implant is further improved by said wall elements.

In a preferred development, that side of the receiving element which lies opposite the end wall is of flattened design in order to form a standing surface.

That is to say, in other words, that the holding and packaging device can therefore also be deposited in such a manner that the longitudinal axis of the receiving element (and therefore the longitudinal axis of the dental implant) is perpendicular to the supporting surface. Further flexibility with regard to the handling is therefore achieved.

In a preferred development, the end wall is provided in the form of at least two, preferably three, segments which at least partially surround the opening.

That is to say, in other words, that the end wall is divided into individual segments which project radially with respect to the opening and are preferably no longer connected to one another but rather are solely mounted on an inner wall of the cylinder. This has the advantage that the elasticity for expanding the opening is further improved.

The end wall or the segments is/are preferably offset inward in the longitudinal direction.

This has the advantage that the inserted tooth implant does not protrude, but rather lies fully within the space surrounded by the cylinder.

Further advantages and refinements of the invention emerge from the description and the attached drawing.

It goes without saying that the features mentioned above and those which have yet to be explained below can be used not only in the respectively stated combination, but also in different combinations or on their own without departing from the scope of the present invention.

BRIEF DESCRIPTION OF THE DRAWINGS

The invention is now explained in more detail using exemplary embodiments and with reference to the drawing, in which.

DETAILED DESCRIPTION OF PREFERRED EMBODIMENTS

Figure 1:
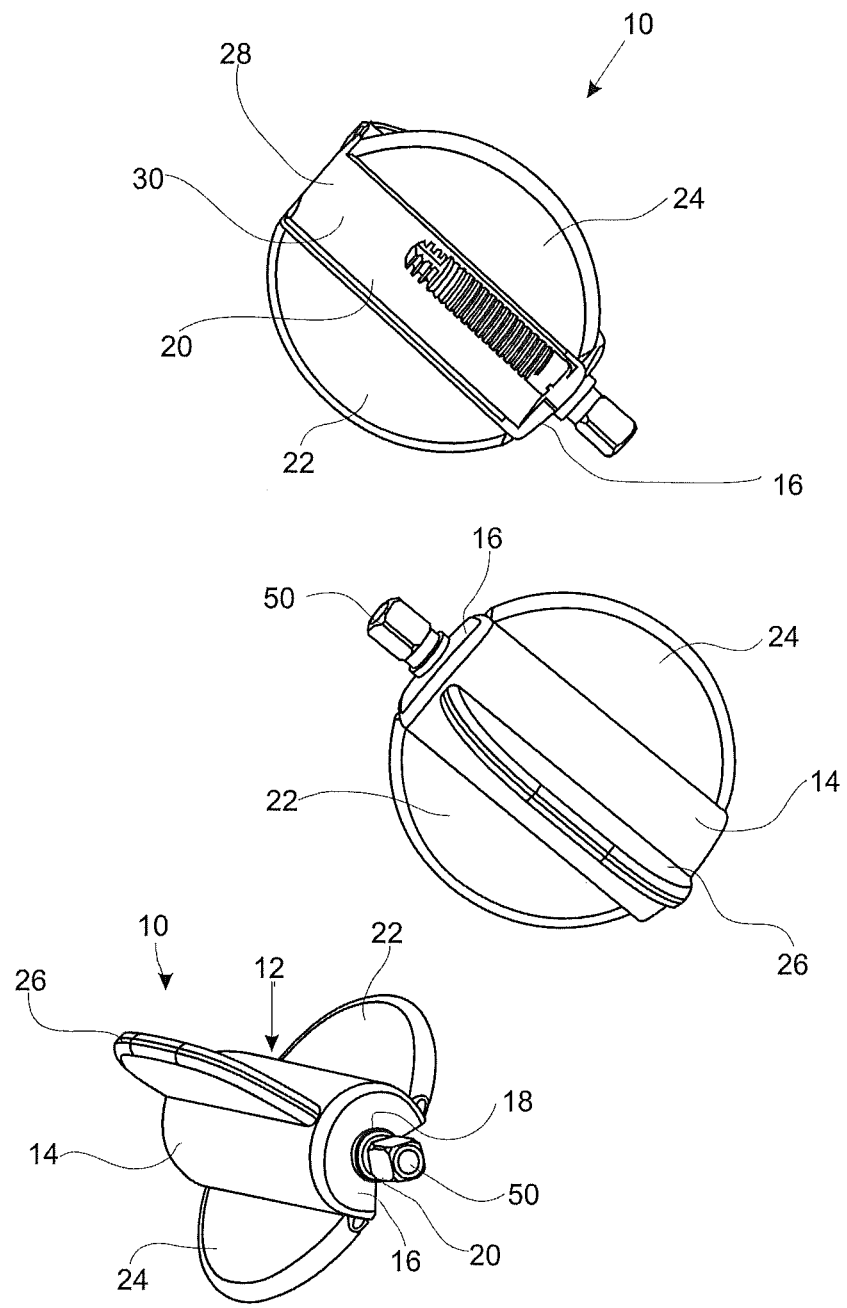
FIG. 1 shows three perspective illustrations of a holding and packaging device according to the invention according to a first embodiment of the invention.

FIG. 1 schematically illustrates a holding and packaging device (called holding device for short below) in three different views, which holding device is identified by the reference number 10. Said holding device 10 serves to receive a dental or tooth implant such that it can subsequently be packaged in a sterile manner. The packaging used can be, for example, a blister packaging.

The holding device 10 comprises an elongate cylindrical receiving element 12 which has a cylinder wall 14 and an end wall 16 at one end of the cylinder wall 14. The cylinder wall 14 extends over an angle (seen in cross section) of more than 180°, but the cylinder wall 14 is not closed in the circumferential direction. An opening 20 which extends over the entire length of the cylinder wall 14 is consequently produced. Said opening 20 can be seen in the top view of FIG. 1.

The cylinder wall 14 accordingly forms—in cross section—a circular segment, but it should be noted at this juncture that the cross section may also have different shapes. The cylinder wall 14 shown in FIG. 1 may also be of polygonal design—in cross section. However, the cylindrical configuration has proven particularly advantageous.

The end wall 16 which has an opening 18 located coaxially with respect to the longitudinal axis of the cylinder wall 14 is mounted at one longitudinal end of the cylinder wall 14. The opening 18 is designed such that it is open at the edge in the direction of the longitudinal opening 20, and therefore a tooth implant 50 can be pressed into the opening.

A total of three grip elements 22, 24, 26 which are placed at a distance of approximately 90° with respect to one another are mounted on the cylinder wall 14. Consequently, the two outer grip elements 22, 24 lie in one plane. The grip elements 22-26 extend in the longitudinal direction over the entire length of the receiving element 12 and have—in top view—a circular segment shape. However, said shape is not essential to the invention, and therefore other shapes are likewise conceivable. It should also be noted at this juncture that the two grip elements do not necessarily have to lie in one plane. On the contrary, they could also run obliquely with respect to one another such that, for example, the angle with respect to the third grip element 26 is in each case greater than 90°.

The holding device 10 shown in FIG. 1 is preferably manufactured from a material, said material preferably being a biocompatible plastic with a certain degree of elasticity. Accordingly, the holding device 10 can be produced cost-effectively by injection molding. The material selected should be a material which can easily be sterilized irrespective of which sterilization method is employed.

In the top illustration of FIG. 1, it can be seen that the tooth implant lies within the receiving space 30 formed by the cylinder wall 14 and does not come into contact here with the surrounding wall. The tooth implant 50 is held within the receiving space 30 via a fixing post which is connected at one end to the dental implant and at the other end is inserted into the opening 18 in the end wall 16. In this case, the opening 18 in the end wall 16 is selected such that the fixing post of the tooth implant 50 is clamped securely in the opening 18. This means, in other words, that the material of the cylinder wall 14 has to have a certain degree of elasticity in order to permit widening of the opening 18 in the end wall 16.

The clamping force exerted on the dental implant or the fixing post can be reduced, for example, by the two grip elements 22, 24, or only one of the two grip elements, being subjected to a force which is approximately in the direction of the third grip element. Such a force has the effect that the cylinder wall 14—as seen in cross section—is widened somewhat such that the opening 20 becomes larger. At the same time, the opening 18 in the end wall 16 is likewise enlarged such that the dental implant can easily be removed from the opening. The same also applies, of course, in the event of the dental implant being introduced into the opening 18, said introduction also being made easier if a force is applied to at least one of the two grip elements 22, 24 in order to widen the opening 18.

Figure 2A:
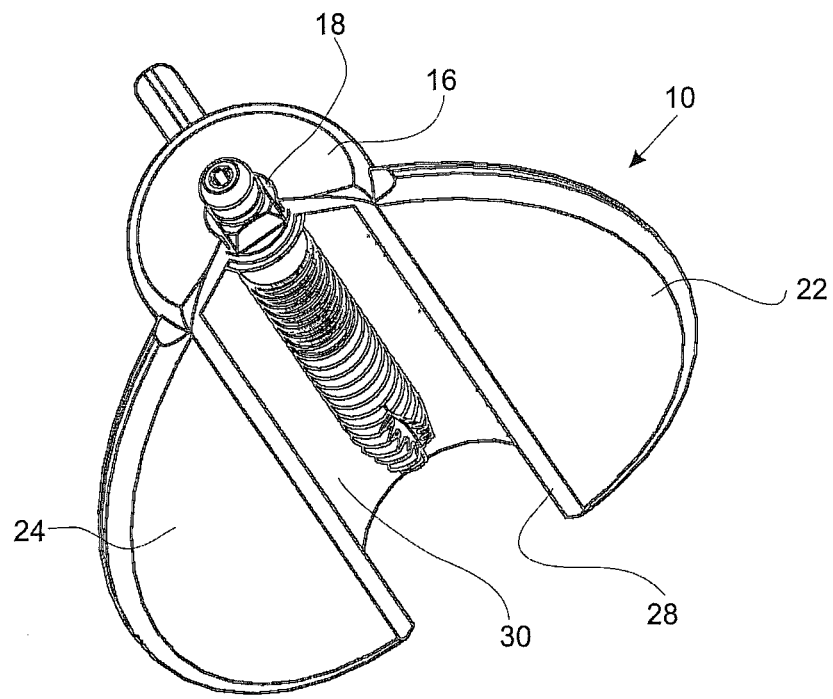
FIGS. 2A and B show two different perspective illustrations of the holding and packaging device according to FIG. 1.
Figure 2B:
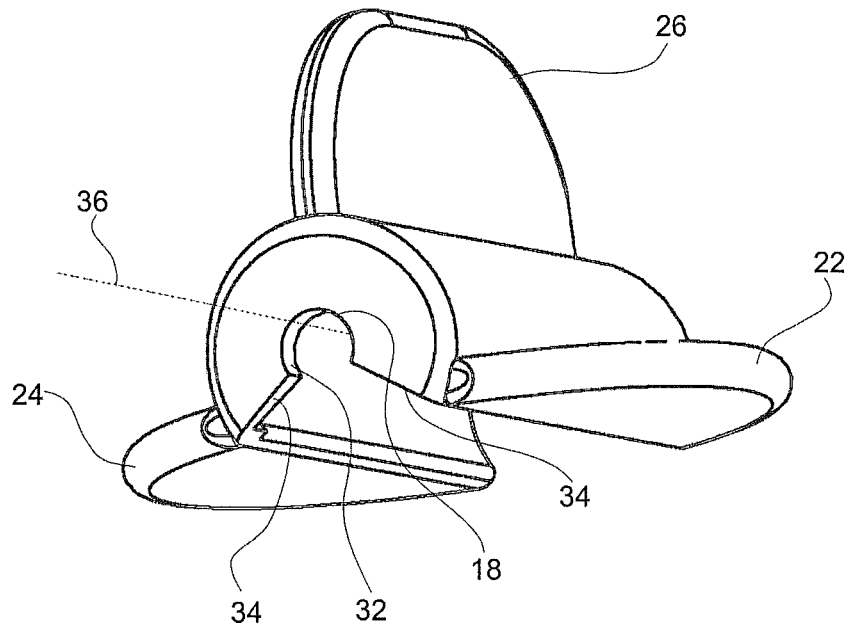

The holding device 10 previously explained in detail is shown once again in detail in FIGS. 2A and 2B. The end wall 16, in which an opening 18 which is open at the edge toward the lower end is provided, can readily be seen here. Said opening 18 lies coaxially with respect to the longitudinal axis 36, for example of the cylinder wall 14. The opening 18 has an edge 32 which extends in the shape of a circular segment over an angle of more than 180° and merges on both sides into a flank 34 which extends rectilinearly with respect to the edge of the cylinder wall 14. This can readily be seen in FIG. 2B.

In contrast to the at least partially closed longitudinal end of the cylinder wall 14, the opposite longitudinal end 28 is of open design. A wall is therefore not present there, and therefore the elasticity of the cylinder wall 14 is not restricted.

Figure 3:
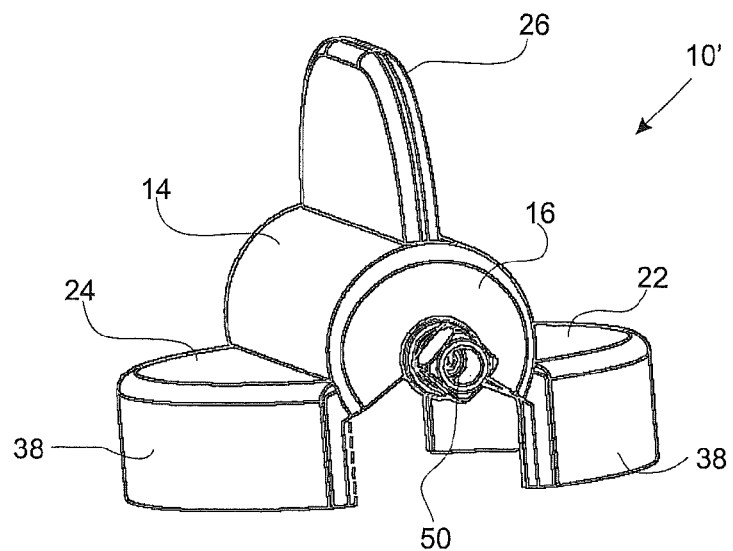
FIG. 3 shows a perspective illustration of a holding and packaging device according to a second embodiment.

A further embodiment of a holding device 10 is illustrated in FIG. 3 and is identified by the reference number 10'. Said holding device 10' substantially corresponds to the holding device already described with respect to FIGS. 1 and 2 and therefore a description of the parts identified by the same reference numbers can be omitted.

The sole difference over the embodiment shown in FIG. 1 is that a respective wall 38 is mounted on the two outer grip elements 22, 24, said wall extending substantially perpendicularly with respect to the corresponding grip element 22, 24 and running along the edge of the grip element 22, 24. The two walls 38 have a semicircular shape, as seen in top view.

Accordingly, when the holding device is placed onto a flat surface, the two grip elements 22, 24 do not rest thereon, but rather the holding device 10' is held at a distance from the surface by the two walls 38.

The advantage here is in particular that an unintentional contact of the dental implant located in the receiving space 30 is further reduced.

Figure 4:
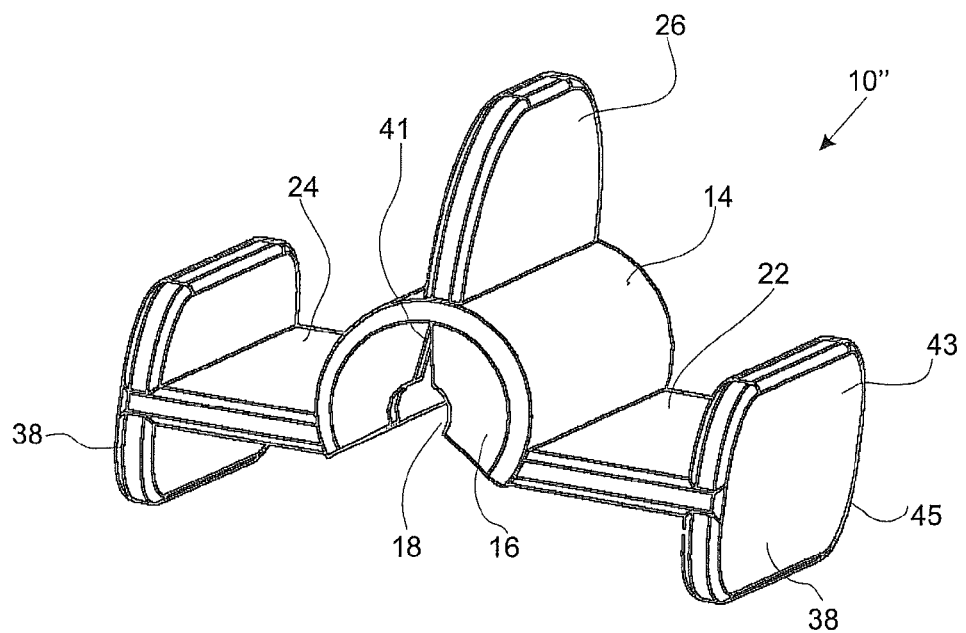
FIG. 4 shows a perspective view of a holding and packaging device according to a third embodiment of the invention.

Finally, a further refinement of a holding device is illustrated in FIG. 4 and is identified by the reference number 10". Said holding device 10" also has substantially the same construction as the holding device 10 according to FIGS. 1 and 2. On account thereof, the parts identified by the same reference numbers are not discussed below.

One of the differences from the holding device 10 explained at the beginning is that the two grip elements 22, 24 are of rectangular design—in top view—and walls 38 running perpendicularly thereto are provided at the end. Said two walls 38 do not only project downward, but also upward in relation to the corresponding grip elements 22 and 24. The grip element 22 or 24 and the respective wall 38 consequently each form a "T". The angle, shown in the figure, of 90° C. between the grip element 22 or 24 and the wall 38 is a preferred configuration, but a different angle may also be selected if the application requires this.

Furthermore, in the region of the opening 18, the holding device 10" has a slot 41 which extends outward in the radial direction from the opening 18, to be precise in the direction of the upper grip element 26. Said slot 41 is of triangular design such that the gap tapers in the radial direction.

Said slot 41 serves to increase the elasticity of the cylinder wall 14 such that the opening 18 can be widened more easily. In order to widen said opening 18, all that is necessary to do is to subject the wall 38 in the upper region 43 to a force directed toward the cylinder wall 14. Furthermore, with the configuration shown in FIG. 4, it is possible to somewhat reduce the opening 18 in diameter in order therefore to increase the clamping force on an inserted dental implant 50. This can be achieved by the two walls 38 being subjected to a force in the lower region 45.

The embodiments shown with respect to FIGS. 3 and 4 are also preferably produced from a biocompatible plastic by injection molding.

Figure 5:
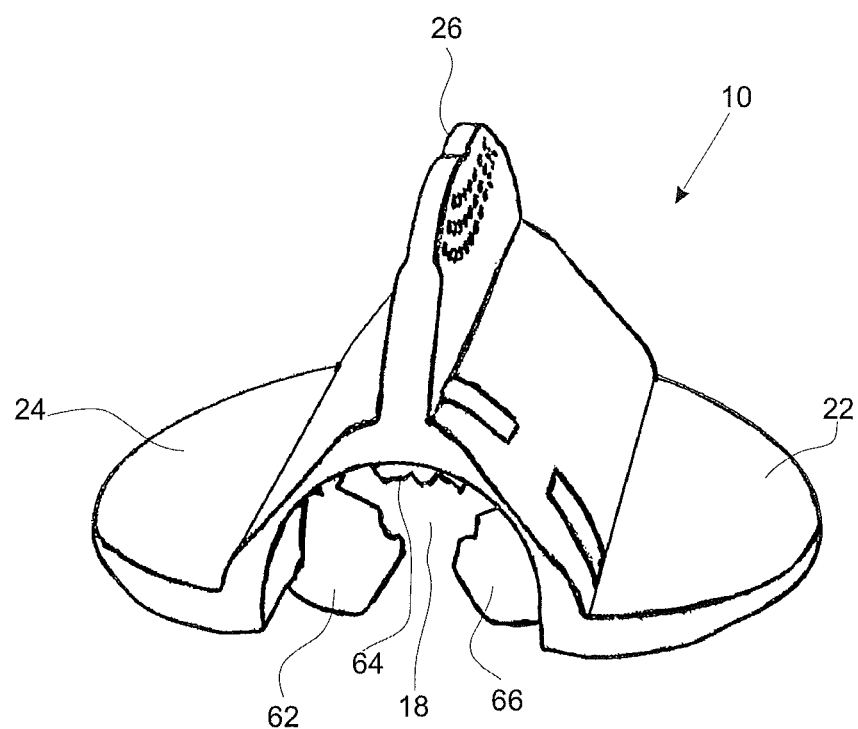
FIG. 5 shows a perspective view of a holding and packaging device according to a further embodiment of the invention.

FIG. 5 illustrates a further embodiment of a holding device 10 which substantially corresponds to that shown in FIG. 1. For this reason, reference is made to the corresponding passages of the description.

A difference over the embodiment shown in FIG. 1 is that the end wall 16 is no longer present. Instead, there are three holding cheeks 62, 64, 66 which are spaced apart in the circumferential direction (with respect to the longitudinal opening 20) and define the opening 18 therebetween. As previously described, an implant can be received and held in said opening. In addition to the "segmentation" of the end wall into three segmental holding cheeks 62, 64, 66, the latter are offset somewhat inward (as seen in the longitudinal direction). This can clearly be seen in FIG. 5. This has the effect that the tooth implant 50 no longer protrudes in relation to the end surface of the holding device, as is the case, for example, in the embodiment shown in FIG. 1. Furthermore, the elasticity is improved by the segmentation of the end wall into individual holding cheeks, and therefore, in particular, the removal of the tooth implant is made easier.

A general feature of all of the holding devices 10 shown is that they protect an inserted dental implant all the way around such that the dental implant does not have any contact with the holding device and there is no contact with and damage to the surface of the dental implant during handling. The dental implant can be deposited in the region of operation in the holding device 10 without the dental implant coming into contact with the support. The dental implant can be manipulated with the holding device 10 in the region of operation without being touched.

The dental implant is removed from the holding device 10 with a tool which is customary for this purpose, with it being possible for the dental implant to be held securely and in a stable manner with the holding device.

The dental implant is removed by the clamping being overcome, or, in the embodiment shown in FIG. 4, by the clamping region being pressed.

What is claimed is:
1. A dental implant holding and packaging device with an elongate cylindrical receiving element having a longitudinal axis and which has a cylinder wall forming a receiving space therein and at least one clamp wall attached to the cylinder wall and arranged substantially perpendicular to said longitudinal axis, wherein the clamp wall has an opening for receiving and holding a tooth implant, and the cylinder wall has a longitudinal opening, wherein
the longitudinal opening permits access to the receiving space and extends over the entire length of the cylinder wall,
at least two grip elements which are mounted opposite each other on the cylinder wall and extend outward are provided, and
the cylinder wall is manufactured from an elastic material such that, by application of a force, the opening in the clamp wall can be widened in order to introduce or remove a tooth implant, wherein the opening in the clamp wall is spaced radially inward from the cylinder wall such that the tooth implant is suspended in said receiving space when held by the clamp wall so that that the tooth implant does not contact the cylinder wall.

2. The dental implant holding and packaging device as claimed in claim 1, wherein the cylinder wall in cross section encloses an angle of at least 180°, and the longitudinal opening in the circumferential direction is at least the same size as the diameter of the tooth implant which is to be inserted.

3. The dental implant holding and packaging device as claimed in claim 1, wherein the grip elements are arranged on the cylinder wall in a manner such that they lie in one plane.

4. The dental implant holding and packaging device as claimed in claim 1, wherein the opening in the clamp wall is designed in the shape of a circular segment and is open at the edge toward the longitudinal opening.

5. The dental implant holding and packaging device as claimed in claim 4, wherein the opening is arranged coaxially with respect to the longitudinal axis of the receiving element.

6. The dental implant holding and packaging device as claimed in claim 4, wherein a slot lying generally opposite the longitudinal opening extends radially from the opening.

7. The dental implant holding and packaging device as claimed in claim 1, wherein the receiving element is manufactured from a flexible plastic.

8. The dental implant holding and packaging device as claimed in claim 1, wherein a further grip element which is arranged between the two other grip elements is provided.

9. The dental implant holding and packaging device as claimed in claim 1, wherein a respective wall element is mounted on the two grip elements, said wall element extending perpendicularly with respect to the grip element and serving as a spacer element.

10. The dental implant holding and packaging device as claimed in claim 1, wherein the side of the receiving element which lies opposite the clamp wall is of flattened design in order to form a standing surface.

11. The dental implant holding and packaging device as claimed in claim 1, wherein the clamp wall is provided in the form of at least two segments which at least partially surround the opening.

12. The dental implant holding and packaging device as claimed in claim 11, wherein the clamp wall includes three segments which are spaced apart uniformly over the inner circumference of the longitudinal opening.

13. The dental implant holding and packaging device as claimed in claim 1, wherein the clamp wall is set back inward in the longitudinal direction.

14. The dental implant holding and packaging device as claimed in claim 7, wherein the receiving element is manufactured from a biocompatible plastic.

* * * * *